United States Patent [19]
Fedorov et al.

[11] 3,945,054
[45] Mar. 23, 1976

[54] THROUGH CORNEAL PROSTHESIS AND METHOD OF INSTALLING SAME

[76] Inventors: Svyatoslav Nikolaevich Fedorov, Novopeschannaya ulitsa, 2a, kv. 40; Viktor Konstantinovich Zuev, Staroe shosse, 10, kv. 12, both of Moscow, U.S.S.R.

[22] Filed: Dec. 2, 1974

[21] Appl. No.: 528,986

Related U.S. Application Data

[63] Continuation of Ser. No. 447,023, Feb. 28, 1974, abandoned.

[30] Foreign Application Priority Data

Mar. 4, 1973    U.S.S.R............................. 1887763

[52] U.S. Cl. ..................................................... 3/13
[51] Int. Cl.² ........................................... A61F 1/16
[58] Field of Search ...................... 3/13, 1; 351/160

[56] References Cited
UNITED STATES PATENTS 2,714,721   8/1955   Stone ......................................... 3/13
3,074,407   1/1963   Moon et al. ........................ 3/13 UX
3,458,870   8/1969   Stone ......................................... 3/13

OTHER PUBLICATIONS

"Implantation of an Artificial Cornea" by Manuel A. Torres, et al. *American Journal of Ophthalmology*, Vol. 56, No. 6, pp. 937–941, Dec. 1963.

*Primary Examiner*—Ronald L. Frinks
*Attorney, Agent, or Firm*—Holman & Stern

[57] ABSTRACT

A through corneal prosthesis is proposed which comprises a bearing member to be introduced between the corneal layers and a bushing with a threaded hole rigidly mounted on the bearing member, the threaded hole threadedly receiving a removable optical cylinder. For the period of implantation of the bearing member, instead of the optical cylinder a temporary removable plug is screwed in the bushing, the height of the bushing and the plug not exceeding the thickness of the cornea, so that the bearing member of the prosthesis is implanted without requiring perforation of the corneal layers.

2 Claims, 8 Drawing Figures

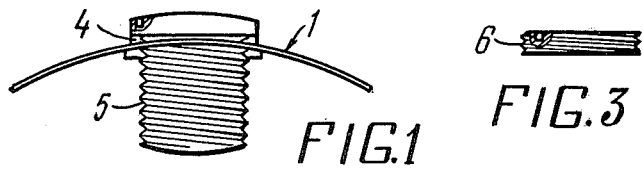
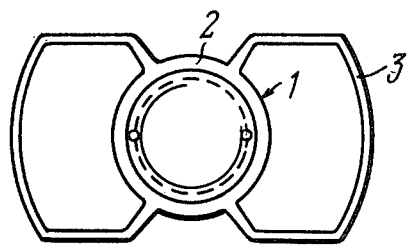
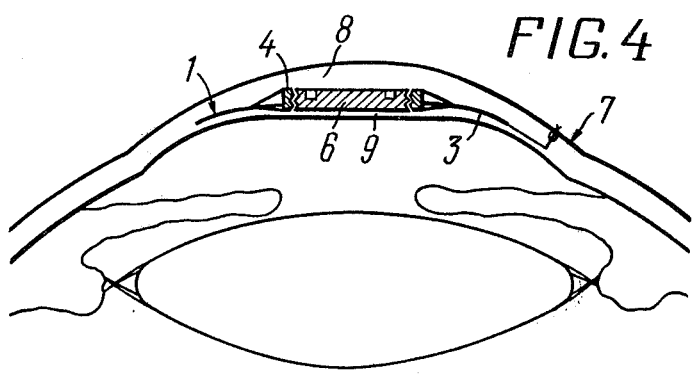

THROUGH CORNEAL PROSTHESIS AND METHOD OF INSTALLING SAME

This is a continuation of application Ser. No. 447,023 filed Feb. 28, 1974, now abandoned.

BACKGROUND OF THE INVENTION

The present invention relates generally to medical technology and more particularly, it relates to through corneal prostheses employed to restore vision to patients with grave cataracts in cases wherein keratoplasty fails.

It is known in the art to employ a through corneal prosthesis comprising a bearing member formed as a disk with a plurality of perforations formed therein carrying a centrally mounted bushing with a threaded hole, and a removable optical cylinder with an external thread threadedly received into the bushing. The known prosthesis is also provided with a temporary removable plug having an external thread corresponding to the thread of the hole in the bushing.

The prosthesis is installed in a two-step operation. At the first step, the cornea is divided into outer and inner layers, the inner layers are perforated and the bearing member whereof the bushing carries the removable plug screwed therein is inserted into the space intermediate the outer and inner layers of the cornea until the bushing is aligned with the perforated hole. The requirement to perforate the inner corneal layers stems from the height of the bushing which far exceeds the thickness of the cornea, whereinto the prosthesis is installed.

After the bearing member of the prosthesis has been installed, a suture is applied.

The second stage of the operation is carried out after the bearing member of the prosthesis has been implanted. This step comprises perforating the outer corneal layers above the bushing and substituting an optical cylinder for the temporary plug.

However, with the inner corneal layers perforated at the first stage of the operation, the adhesion of the divided corneal layers is more difficult to achieve and the implantation of the bearing portion is hindered. Further, the perforation provides a route whereby moisture from the anterior chamber may seep into the space between the corneal layers, giving rise to a "false" chamber.

SUMMARY OF THE INVENTION

It is an object of the present invention to provide a through corneal prosthesis which will ensure reliable adhesion of the divided corneal layers, thereby securely immobilizing the prosthesis.

It is another object of the present invention to provide a prosthesis which will render the operation of prosthesis installation less traumatic.

It is a further object of the present invention to provide a prosthesis which will ensure that the anterior chamber is securely sealed off.

The foregoing objects are attained by that in a through corneal prosthesis, comprising a bearing member to be introduced into the space between the corneal layers, a bushing with a threaded hole rigidly secured on the bearing member, with a temporary removable plug threadedly received into the threaded hole of the bushing while the bearing member is being implanted into the cornea, and also a removable optical cylinder with a thread which is screwed in the bushing instead of the plug after the bearing member has been implanted into the cornea, in accordance with the invention, the height of the bushing and of the plug does not exceed the thickness of the cornea whereinto the prosthesis is installed.

It is desirable that the bearing member should be formed as a ring with two frames arranged diametrically thereon.

The method of installing the proposed prosthesis includes two steps, the first one of which, in accordance with the invention, comprises dividing the cornea into inner and outer layers, placing the bearing member with the plug screwed in the bushing therebetween, and applying a suture; after the bearing member has been implanted, the second step is carried out which comprises, in accordance with the invention, perforating the outer layers of the cornea above the bushing, removing the plug, perforating the inner layers of the cornea beneath the bushing, and screwing the optical cylinder therein.

The proposed through corneal prosthesis obviates the need to perforate the inner corneal layers at the first step of the operation, viz. while implanting the bearing member of the prosthesis with the plug, so that perforation is done at the second step of the operation, i.e. while substituting the optical cylinder for the plug, which provides for reliable implantation of the bearing member of the prosthesis and seals off the anterior chamber.

While installing the proposed prosthesis, the diameter of the perforated hole in the inner layers of the cornea is equal to the diameter of the optical cylinder, whereas with the prior prosthesis the diameter of the perforated hole must be equal to the diameter of the bushing wherein the optical cylinder is screwed. With the perforated hole being of a smaller diameter, the proposed prosthesis seals off the anterior chamber more effectively than the prior prosthesis, and the probability of secondary infection of the eye is thereby minimized.

The generally rectangular overall configuration of the bearing member formed as a ring with two frames ensures secure implantation and minimizes surgical trauma.

BRIEF DESCRIPTION OF THE DRAWINGS

The invention will be better understood from the following description of an exemplary embodiment thereof taken in conjunction with the accompanying drawings, wherein:

FIG. 1 is a view, partially in section, of a through corneal prosthesis, in accordance with the invention;

FIG. 2 is a plan view of FIG. 1;

FIG. 3 illustrates a removable temporary plug, in accordance with the invention;

FIG. 4 shows the position of the bearing member of the prosthesis with the plug after the first stage of the prosthesis installation operation, in accordance with the invention;

DETAILED DESCRIPTION OF THE PREFERRED EMBODIMENT

Figure 5:
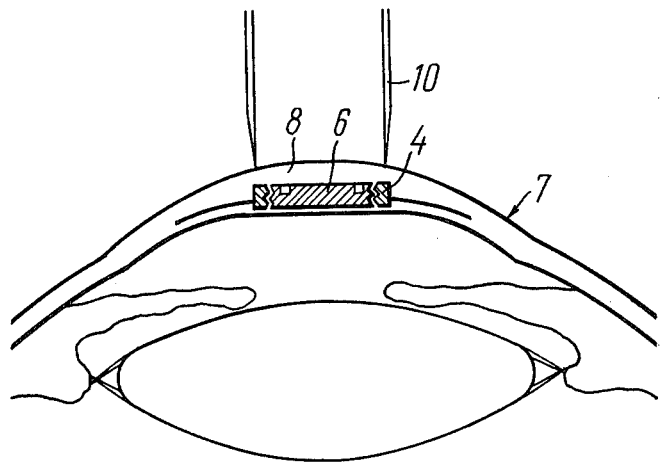
FIGS. 5, 6 and 7 illustrate the second stage of prosthesis installation, in accordance with the invention.

Referring now to the drawings, it can be seen to be illustrated therein a through corneal prosthesis comprising a bearing member 1 (FIG. 1) formed as a ring 2 (FIG. 2) with two frames 3 diametrically arranged thereon so as to provide the bearing member with a generally rectangular overall shape. Rigidly mounted on the bearing member 1 is a bushing 4 (FIG. 1) with a threaded hole whereinto a removable optical cylinder 5 provided with an external thread is threadedly received. The prosthesis is also provided with a temporary removable plug 6 (FIG. 3) having an external thread corresponding to the thread of the hole formed in the bushing 4 (FIG. 1). The height of the bushing 4 and the plug 6 (FIG. 4) does not exceed the thickness of cornea 7 whereinto the prosthesis is installed.

The through corneal prosthesis of this invention is installed in a two-step operation which is carried out as follows.

At the first step, the cornea 7 is divided into outer layers 8 and inner layers 9 spaced by a distance equal to the width of the frames 3.

The bearing member 1 whereof the bushing 4 carries the removable temporary plug 6 screwed therein is placed between the layers 8 and 9.

The small height of the bushing 4 permits installing the bearing member 1 between the outer layers 8 and the inner layers 9 of the cornea 7 without perforating same, providing for effective implantation of the bearing member 1 of the prosthesis.

After the bearing member 1 of the prosthesis has been installed, a suture is applied.

With the suture applied, the first step of the prosthesis installation operation is over.

Figure 6:
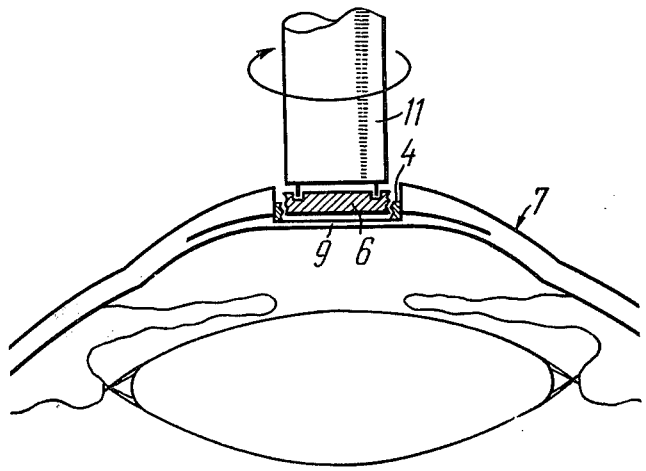
Figure 7:
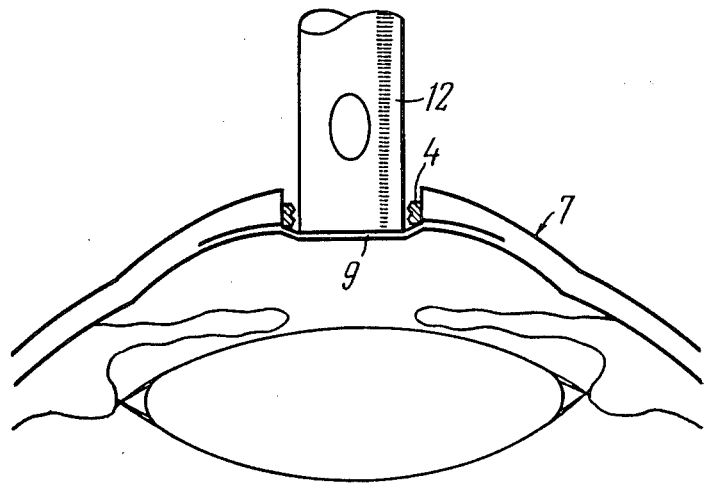
Figure 8:
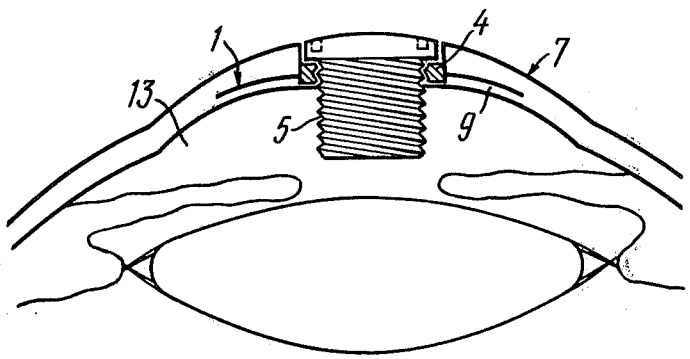
FIG. 8 shows the position of an installed prosthesis in the cornea, in accordance with the invention.

Three or four months later, after the bearing member 1 of the prosthesis has been implanted, the second step of the prosthesis installation operation is carried out. It comprises perforating the outer layers 8 of the cornea 7 above the bushing 4 by means of a trepan 10 (FIG. 5), then by use of a special key 11 (FIG. 6) removing the plug 6, perforating the inner layers 9 with a trepan 12 (FIG. 7), and then screwing the removable optical cylinder 5 (FIG. 8) in the bushing 4. This done, the operation is over.

At the second step of the operation, when screwing the optical cylinder 5, the latter's thread comes into close contact with the edges of the perforated hole formed in the inner layers 9 of the cornea 7, thereby providing for the water-tightness of an anterior chamber 13.

What we claim is:

1. A through corneal prosthesis, comprising: a bearing member to be introduced between the layers of the cornea whereinto said prosthesis is installed; a bushing having a threaded hole rigidly mounted on said bearing member, the height of said bushing not exceeding the thickness of the cornea whereinto said prosthesis is installed; and a removable temporary threaded plug which is threadedly received into said hole of said bushing when said bearing member is being implanted, the height of said plug corresponding to the height of said bushing and not exceeding the thickness of the cornea whereinto the prosthesis is installed, said plug being adapted to be removed after said bearing member has been implanted and to be replaced by a removable threaded optical cylinder threadedly receivable into said hole of said bushing, said bearing member being formed as a ring having two frames which are diametrically arranged thereon so as to provide said bearing member with a generally rectangular overall shape.

2. A method of installing a through corneal prosthesis comprising a bearing member with a bushing, a removable temporary plug threadedly received into said bushing, and a removable optical cylinder screwed into said bushing instead of said plug after said bearing member has been implanted, which includes two steps, the first step thereof comprising dividing the cornea into outer and inner layers, placing said bearing member of the prosthesis with said plug screwed into said bushing thereof between said outer and inner layers and applying a suture; and after said bearing member has been implanted, the second step of prosthesis installation is performed which comprises perforating said outer layer of the cornea above said bushing, removing said plug, perforating said inner corneal layer beneath said bushing and screwing said optical cylinder therein.

* * * * *